United States Patent
Smith et al.

(10) Patent No.: US 7,140,366 B2
(45) Date of Patent: *Nov. 28, 2006

(54) EXPIRATORY LIMB FOR A BREATHING CIRCUIT

(75) Inventors: Daniel John Smith, Auckland (NZ); Gavin Walsh Millar, Auckland (NZ); Kevin Blake Powell, Auckland (NZ); David Peter Baldwin, Auckland (NZ)

(73) Assignee: Fisher & Payke Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 10/622,755

(22) Filed: Jul. 18, 2003

(65) Prior Publication Data

US 2004/0099268 A1   May 27, 2004

Related U.S. Application Data

(62) Division of application No. 09/850,797, filed on May 8, 2001, now Pat. No. 6,769,431.

(30) Foreign Application Priority Data

May 10, 2000 (NZ) ........................ 504439
Dec. 20, 2000 (NZ) ........................ 509041

(51) Int. Cl.
*A61M 15/00* (2006.01)

(52) U.S. Cl. ................ 128/203.16; 128/203.17

(58) Field of Classification Search ................ 128/911, 128/912, 204.18, 204.17, 200.24, 201.13, 128/203.16, 203.17, 203.26, 203.12, 205.12, 128/200.18, 200.14, 203.27; 156/428; 138/129
See application file for complete search history.

(56) References Cited

U.S. PATENT DOCUMENTS

| 3,144,313 A | 8/1964 | Pfefferle |
| 3,228,877 A | 1/1966 | Mahon |
| 3,245,206 A | 4/1966 | Bonnet |
| 3,292,346 A | 12/1966 | Adams |

(Continued)

FOREIGN PATENT DOCUMENTS

EP   0557040   8/1993

(Continued)

OTHER PUBLICATIONS

One page off the Perma Pure Inc. website of the product brochure #104 of the New PD™ -Series Gas Dryers.

(Continued)

*Primary Examiner*—Teena Mitchell
(74) *Attorney, Agent, or Firm*—Trexler, Bushnell, Giangiorgi, Blackstone & Marr, Ltd.

(57) ABSTRACT

A breathing circuit component includes an inlet, an outlet and an enclosing wall. The enclosing wall defines a gases passageway between the inlet and the outlet. At least a region of the enclosing wall is formed from a breathable material that allows the passage of water vapor without allowing the passage of liquid water or respiratory gases. The breathing circuit component may be the expiratory limb of a breathing circuit.

18 Claims, 9 Drawing Sheets

U.S. PATENT DOCUMENTS

| | | |
|---|---|---|
| 3,303,105 A | 2/1967 | Konikoff |
| 3,307,330 A | 3/1967 | Niedzleiski et al. |
| 3,367,850 A | 2/1968 | Johnson |
| 3,434,471 A | 3/1969 | Liston |
| 3,735,558 A | 5/1973 | Skarstrom et al. |
| 3,735,559 A | 5/1973 | Salemme |
| 3,856,051 A | 12/1974 | Bain |
| 3,889,717 A | 6/1975 | Obadal et al. |
| 3,891,556 A | 6/1975 | Richardson et al. |
| 3,895,630 A | 7/1975 | Bachman |
| 3,910,808 A | 10/1975 | Steward |
| 3,963,856 A | 6/1976 | Carlson et al. |
| 3,966,525 A | 6/1976 | Steward |
| 4,007,737 A | 2/1977 | Paluch |
| 4,048,993 A | 9/1977 | Dobritz |
| 4,204,562 A | 5/1980 | Kelly |
| 4,207,457 A | 6/1980 | Haglund et al. |
| 4,265,235 A | 5/1981 | Fukunaga |
| 4,265,239 A | 5/1981 | Fischer, Jr. et al. |
| 4,327,775 A | 5/1982 | Tally |
| 4,336,798 A | 6/1982 | Beran |
| 4,337,800 A | 7/1982 | Carlson et al. |
| 4,343,672 A | 8/1982 | Kanao |
| 4,420,016 A | 12/1983 | Nichols |
| 4,456,034 A | 6/1984 | Bixby |
| 4,462,397 A | 7/1984 | Suzuki |
| 4,463,755 A | 8/1984 | Suzuki |
| 4,469,495 A | 9/1984 | Hiraizumi et al. |
| 4,490,575 A | 12/1984 | Kutnyak |
| 4,509,359 A | 4/1985 | Gedeon et al. |
| 4,653,542 A | 3/1987 | Tascher |
| 4,686,354 A | 8/1987 | Makin |
| 4,698,890 A | 10/1987 | Neaves |
| 4,705,543 A | 11/1987 | Kertzman |
| 4,708,831 A | 11/1987 | Elsworth et al. |
| 4,791,963 A | 12/1988 | Gronert et al. |
| 4,808,201 A | 2/1989 | Kertzman |
| 4,844,719 A | 7/1989 | Toyomoto et al. |
| 4,875,908 A | 10/1989 | Kikukawa et al. |
| 4,967,744 A | 11/1990 | Chua |
| 5,042,500 A | 8/1991 | Norlien et al. |
| 5,046,531 A | 9/1991 | Kanao |
| 5,160,511 A | 11/1992 | Lovelock |
| 5,233,996 A | 8/1993 | Coleman et al. |
| 5,284,160 A | 2/1994 | Dryden |
| 5,357,948 A | 10/1994 | Eilentropp |
| 5,454,061 A | 9/1995 | Carlson |
| 5,461,122 A | 10/1995 | Yilgor et al. |
| 5,501,212 A | 3/1996 | Psaros |
| 5,620,500 A | 4/1997 | Fukui et al. |
| 5,637,168 A | 6/1997 | Carlson |
| 5,640,951 A | 6/1997 | Huddart et al. |
| 5,798,013 A | 8/1998 | Brandenburger |
| 5,848,223 A | 12/1998 | Carlson |
| 5,894,839 A | 4/1999 | Rosenkoetter et al. |
| 5,975,144 A | 11/1999 | Akedo et al. |
| 5,983,896 A | 11/1999 | Fukunaga et al. |
| 6,078,730 A | 6/2000 | Huddart et al. |
| 6,148,818 A | 11/2000 | Pagan |
| 6,167,883 B1 | 1/2001 | Beran et al. |
| 6,367,510 B1 | 4/2002 | Carlson |
| 6,394,145 B1 | 5/2002 | Bailly |
| 6,432,169 B1 | 8/2002 | Kluwe et al. |
| 6,523,538 B1 | 2/2003 | Wikefeldt |
| 6,536,428 B1 | 3/2003 | Smith et al. |
| 2002/0002976 A1 | 1/2002 | Smith et al. |
| 2002/0195104 A1 | 12/2002 | Fini et al. |
| 2003/0028139 A1 | 2/2003 | Inoue |
| 2003/0070680 A1* | 4/2003 | Smith et al. ............ 128/204.17 |

FOREIGN PATENT DOCUMENTS

| | | |
|---|---|---|
| EP | 621050 | 4/1994 |
| GB | 2139110 | 8/1983 |
| GB | 2252515 | * 12/1992 |
| JP | 62236724 | 10/1987 |
| JP | 5052378 | 3/1993 |
| JP | 200024111 | 1/2000 |
| WO | WO9718001 | 5/1997 |

OTHER PUBLICATIONS

Three pages off the SympaTex website of some of the most common questions that are asked and some technical data on the SympaTex membrane.

Australian Patent Application No. 200143823 Published on Nov. 15, 2001 entitled Components for Breathing Circuits; Inventors Smith, Baldwin, Powell and Millar.

* cited by examiner

EXPIRATORY LIMB FOR A BREATHING CIRCUIT

This application is a divisional application of U.S. patent application Ser. No. 09/850,797, filed on May 8, 2001, now U.S. Pat. No. 6,769,431, issued on Aug. 3, 2004.

BACKGROUND TO THE INVENTION

1. Field of the Invention

The present invention relates to components for breathing circuits and in particular to components for use in the expiratory arm of a breathing circuit.

2. Summary of the Prior Art

In assisted breathing, particularly in medical applications, gases having high levels of relative humidity are supplied and returned through conduits of a relatively restricted size. Build up of condensation on the inside wall of the conduit is a frequent result of this high humidity. In the prior art, attempts have been made to reduce the adverse effect of this condensation by either reducing the level of condensation or providing collection points in the conduit for draining condensed liquid from the conduit. Reducing the condensation has generally been by maintaining or elevating the temperature of the gases flow and/or of the conduit wall to reduce the formation of condensation.

SUMMARY OF THE INVENTION

It is an object of the present invention to provide a component, with particular application to the expiratory limb of a breathing circuit, which will at least go some way towards improving on the above or which will at least provide the public and the medical profession with a useful choice.

In a first aspect the invention consists in a breathing circuit limb including an inlet, an outlet and an enclosing wall defining a substantially singular exhalation flow passage between said inlet and said outlet, at least a region of said enclosing wall being of a material that allows the passage of water vapour without allowing the passage of liquid water or respiratory gases, and a water vapour flow path from said exhalation flow passage to ambient air through said material.

In a further aspect the invention consists in a breathing circuit limb having both inspiratory and expiratory gases passageways, each having a respective inlet and outlet and a wall defining a gases passageway extending from said inlet to said outlet, at least a region of the wall of the expiratory conduit being of a material that allows the passage of water vapour without allowing the passage of liquid water or respiratory gases, and a water vapour flow path from said exhalation flow passage to ambient air through said material.

In a still further aspect the invention consists in apparatus for forming a breathing circuit conduit comprising or including:

a former, onto which a tube wall can be deposited and which advances said deposited tube wall in an advance axis and rotates said deposited tube wall about said advance direction, the speed of said advance and the speed of said rotation together defining a pitch, at least one film laying head which deposits a film on said former, the combined width of said film deposited by said film laying heads being wider than said pitch such that adjacent turns of laid film overlap to form an overlap seam, a bead laying head for each said film laying head, each said bead laying head laying a reinforcing bead on an overlap seam, an axial thread laying head, said thread laying head fitted over and around said former and carrying a plurality of thread feeds, each thread feed allowing the drawing of a thread from a reserve, and a rotator to rotate said axial thread laying head at substantially the same speed as the expected rotation speed of said tube.

Hereinafter, throughout the description, a material that allows the passage of water vapour without allowing the passage of liquid water or respiratory gases is described as a "breathable" material. Materials may be breathable due to their composition, physical structure a combination thereof.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

Figure 1:
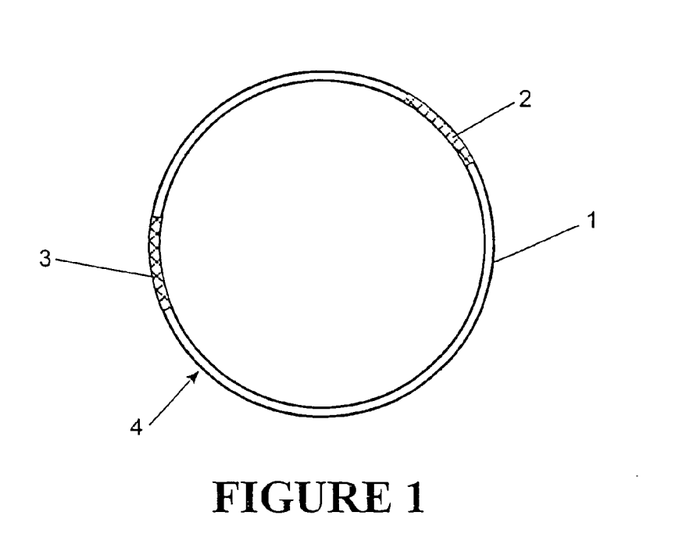
FIG. 1 is a cross sectional elevation of a conduit for the expiratory limb of a breathing circuit according to one embodiment of the present invention.

Referring to FIG. 1 in one embodiment of the invention the conduit 4 of the expiratory limb of a breathing circuit is formed having one or more longitudinal strips 2, 3 of breathable membrane as part of the wall 1 thereof.

One possible material for the breathable regions is an activated perfluorinated polymer material having extreme hydrophilic properties. An example of this polymer material is marketed under the trade name NAFION® by DuPont Fluoro products of Fayetteville USA. This material is useful due to its extreme hydrophilic properties and due to its ability to be extruded, particularly to be co-extruded in combination with other plastic materials.

Alternative materials are also envisaged including:
(a) Hydrophilic thermoplastics,
(b) woven treated fabric products exhibiting breathable characteristics The preferred material is a hydrophilic polyester block copolymer formed into a homogeneous flat film. An example of such a film is sold under the brand SYMPATEX®. This material is particularly suited to thin film productions.

Figure 6:
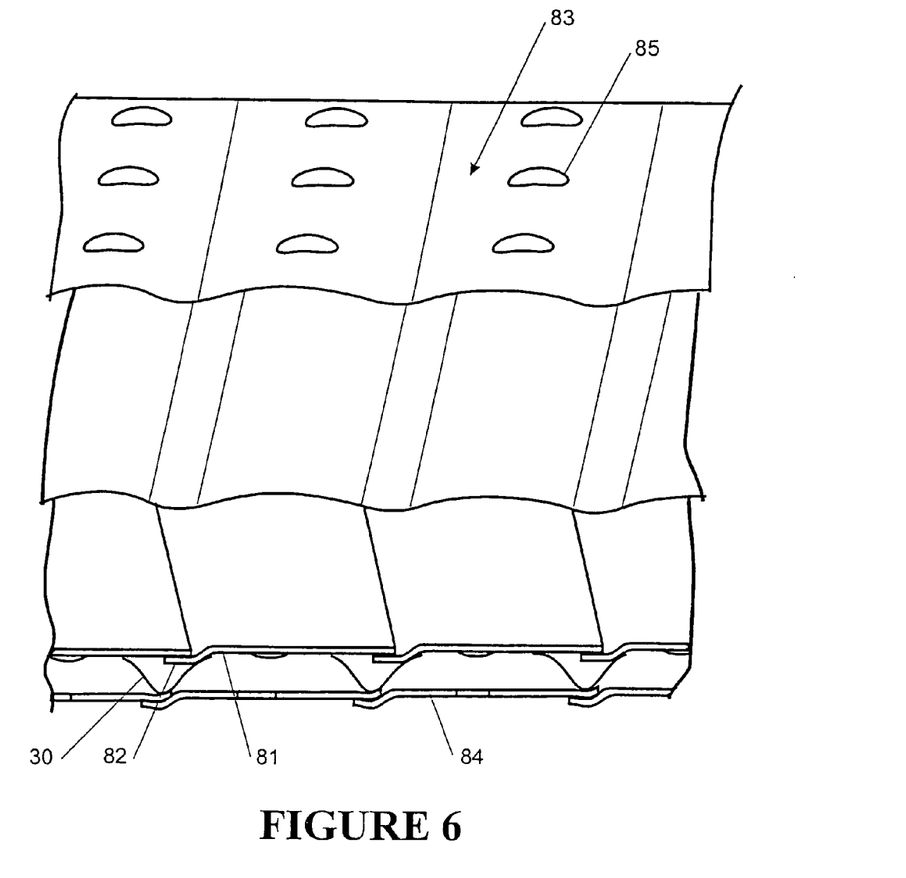
FIG. 6 is a side elevation partially in cross section of an expiratory limb conduit according to a further embodiment of the present invention.

Referring to FIG. 6 an alternative embodiment of the expiratory limb is shown in which the entire flexible wall membrane of the conduit is formed from a breathable plastic membrane, extruded and wound helically with edges of adjacent turns sealed to one another.

Further variations on the embodiment of FIG. 6 are depictured in FIGS. 9a to 9i, 7 and 8. In these figures the flexible wall membrane of the conduit is supplemented by reinforcing to provide resistance to lateral crushing and to longitudinal stretching of the conduit. Further variations are shown including variants having multiple breathable plastic membranes. Apparatus for forming such conduits is described with reference to FIGS. 10, 111 and 12.

Figure 4:
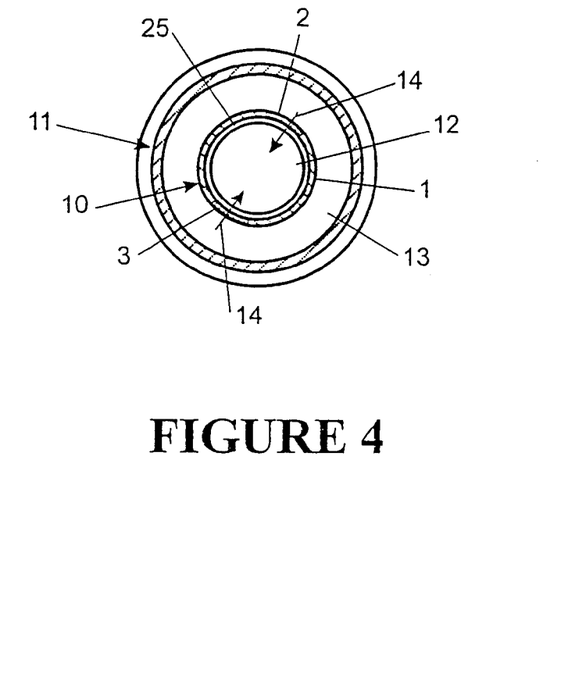
FIG. 4 is a cross sectional elevation of a coaxial breathing circuit according to a further embodiment of the present invention and incorporating a conduit in accordance with the present invention.
Figure 5:
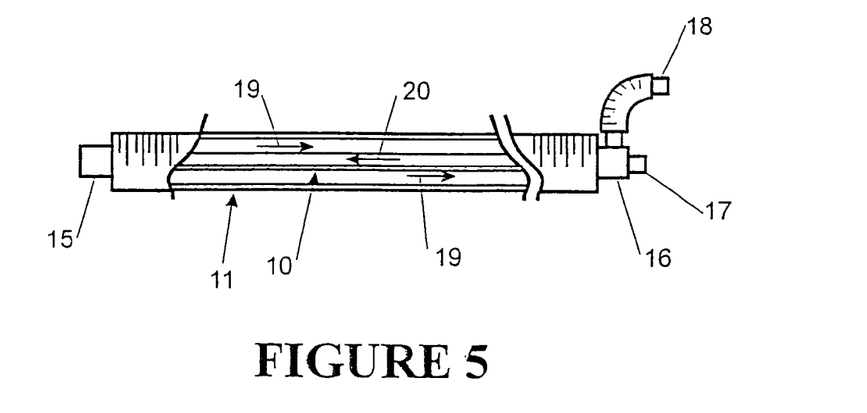
FIG. 5 is a side elevation in partial cross section of the coaxial breathing circuit of FIG. 4.

Referring to FIGS. 4 and 5 a further aspect of the present invention is shown in which an expiratory limb conduit according to the present invention is provided as the inner conduit of a coaxial conduit configuration, such that expiratory gases and inspiratory gases each flow in one of the inner conduit or the space between the inner conduit and the outer conduit and in use water vapour but not liquid water is transmitted from the expiratory gases passageway to the inspiratory gases passageway.

A further component that may usefully include the present invention is a catheter mount. The application of the invention to a catheter mount is described with reference to FIG. 13.

It would be possible alternatively, to have one or more longitudinal sections (lengths) of the conduit being formed of the breathable material or isolated regions of the conduit wall being formed from the material. However the embodiments described herein are preferred due to their apparent simplicity of manufacture, being capable of linear manufacture, either by continuous stitching, gluing or welding, by co extrusion or by winding onto a former.

As a corollary of material cost it is preferred that the conduit wall be manufactured to have a relatively low wall thickness, so much so that the conduit wall membrane may be insufficiently sturdy to be self supporting.

Referring to FIGS. 2, 6, 9a to 9i, 7 and 8, a spiral or helical internal (or external) reinforcing members, or a series of annular hoop reinforcing members, may be provided outside (or inside) the tubular membrane to provide support. The helical, spiral or hoop supporting members may for example be formed from polymer plastic materials, such as the material used in the wall of the conduit (not being the breathable regions), or alternatively may for example be a metal wire support, such as drawn steel wire.

Figure 2:
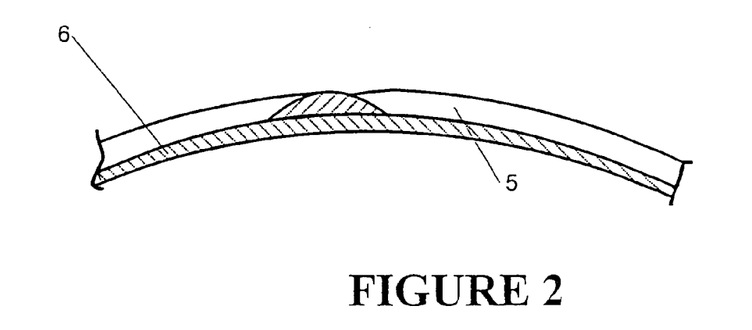
FIG. 2 is a cross sectional view of a section of conduit wall according to one possible construction.

The conduit shown in FIG. 2 may be formed in any one of a number of methods. For example the tubular membrane may be supplied in a continuous tube. Alternatively it might be supplied in tape form, which may result in the conduit of FIG. 6. Supplied as extruded tape, the membrane may be wound helically onto a former. The helical supporting rib, provided in a semi molten state is then laid on the overlap between adjacent turns. The heat from the helical supporting rib bonds the two adjacent strips with the rib forming a flexible resilient conduit once cooled.

Referring to FIG. 6 an additional sheathing layer 83 may be provided over the outside of the conduit. The sheathing layer 83 is supported on the apexes of the ribs 30. The sheathing layer 83 may be a further strip or tape of extruded plastic film wound helically onto the conduit formed on the former. This additional sheath may have a number of purposes and benefits. The sheathing layer 83 may be formed to provide additional strength, reinforcement and protection, for example by selecting an appropriate material or by selecting an appropriate material thickness. The material may be a breathable material, such as that which may be the basis of the inner conduit wall or may be formed from a less expensive non-permeable material. In that case a series of holes or perforations 85 are preferably provided along the strip or tape 84 to provide egress of water vapour or collected condensed water. The holes or perforations 85 may advantageously be formed by pricking holes in the tape 84 using a heated lance during the forming process. Shrinking of the plastic film away from the heated lance has been found to produce consistent and suitably sized holes with an annulus of built up material providing reinforcing at the lip of the hole. The sheath 83, in addition to providing reinforcement and protection for the inner conduit, also provides a barrier to air flow over the inner conduit thereby providing an insulating effect. The insulating effect is greater where there are no perforations 85 through the sheath 83.

Referring to FIGS. 9a–9i it has been found that one of the difficulties with using a breathable membrane such as a SYMPATEX® membrane is its low elastic yield strength. Accordingly under longitudinal force the SYMPATEX® membrane may be easily stretched non-elastically leading to loss of aesthetic appearance and a constriction in the tube diameter. The multiple walled embodiment described with reference to FIG. 6 goes some way toward overcoming this difficulty, providing as it does a second layer of breathable material. Furthermore in the perforated form the outer plastic membrane may be formed from a plastic material having a greater elastic yield strength than the preferred SYMPATEX® membrane.

An alternative structure may be used as a longitudinal reinforcement for the tube. This reinforcement is preferably provided in a form of an additional sheath having an open or mesh structure. For example the sheath may be provided by a plurality of parallel extruded polymer threads running parallel to the axis of the conduit, a plurality of extruded polymer-threads braided or similarly arranged about the conduit and having a substantial axial component in their direction, or by a pre-formed or continuously formed mesh, formed to make a sheath in a similar fashion to the method used for forming the breathable wall. Such a mesh material may be produced by forming a non-woven or woven mesh of individual polymer threads or by stretching a micro perforated sheet to make an expanded mesh, or by other suitable processes. Part or each of these processes may be conducted at the time of, or immediately preceding, using the mesh in forming the reinforcing sheath.

Figure 7:
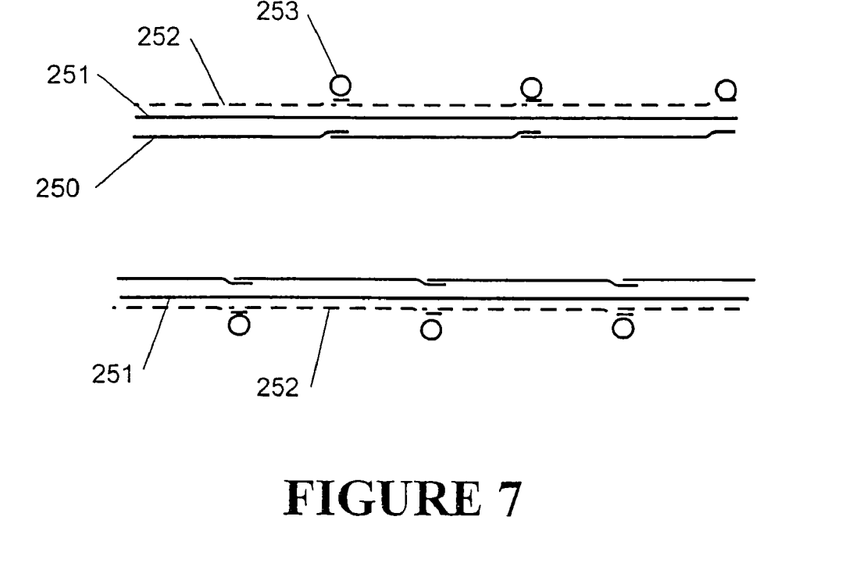
FIG. 7 is a cross sectional side elevation of an expiratory limb for a breathing circuit according to a further embodiment of the present invention.
Figure 8:
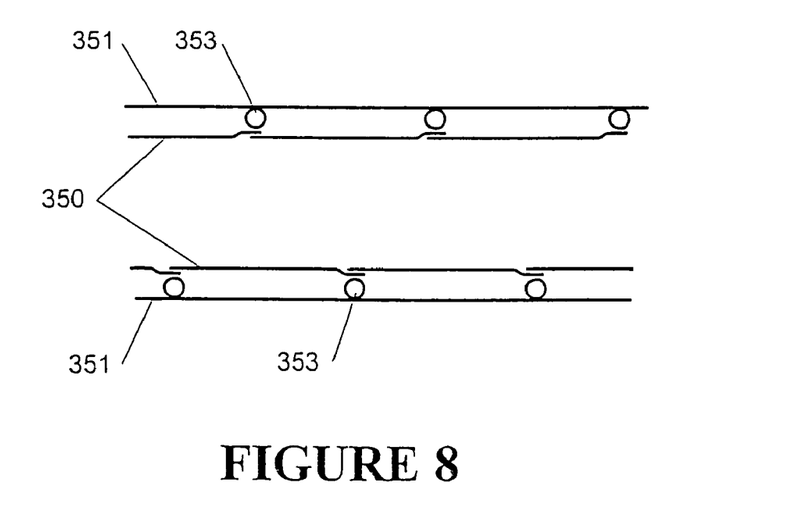
FIG. 8 is a cross sectional side elevation of an expiratory limb for a breathing circuit according to a still further variant, FIGS. 9a–9i demonstrate a range of conduit constructions including longitudinal reinforcement of varying types.

A variety of alternative conduit embodiments incorporating a reinforcing sheath, such as introduced above, are depicted in FIGS. 9a to 9i. Two other preferred forms are depicted in FIGS. 7 and 8. These embodiments have various advantages and/or disadvantages.

Figure 9A:
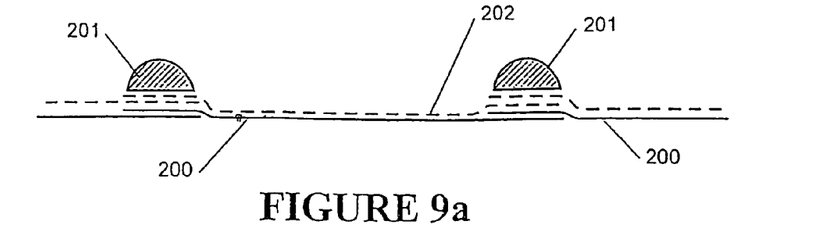

Referring to FIG. 9a a conduit is formed from an extruded tape 200 helically wound on a former to form the breathable wall. A mesh sheath 202 is formed from a mesh tape helically wound onto the outside of the breathable membrane 200. The overlapping edges of the mesh tape and the breathable membrane tape coincide and a molten plastic bead 201 is laid along these edges. The molten bead preferably provokes thermal bonding of all four coinciding layers, two of breathable membrane and two of polymer mesh. It will be appreciated that the polymer mesh may be on the inside or outside of the breathable membrane. However it is preferred that the internal surface of the conduit wall be smooth and hence it is preferred that the mesh tape be applied to the outside of the breathable membrane. It will be appreciated that each turn of mesh tape may be applied directly over each turn of breathable membrane contemporaneously so that the edges of adjacent turns overlap an edge of mesh tape comes between the edges of adjacent turns of breathable membrane tape, which is alternative to how it is depicted in FIG. 9a. It will also be appreciated that either or both of the breathable membrane tape and the mesh tape may be formed contemporaneously with forming the conduit therefrom and the mesh and membrane may accordingly bond over some or all of their contacting surfaces in addition to bonding achieved by heat from the bead 201.

Figure 9B:
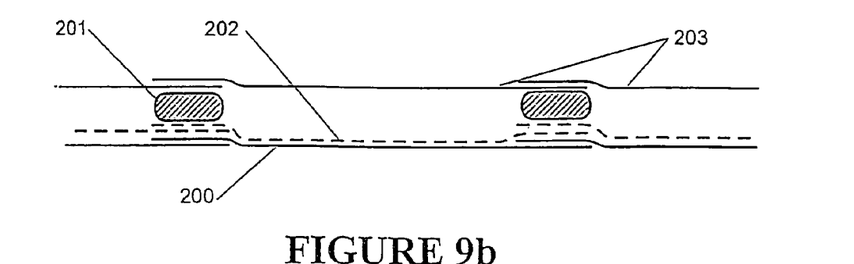

Referring to FIG. 9b a conduit is formed having the same construction of breathable membrane 200, mesh 202 and bead 201. In addition a further sheath of breathable membrane 203 may be applied to the outside of the conduit, with the edges of adjacent turns 203 pressed onto and bonded to the outside of bead 201. This provides additional thermal insulation while allowing for dehumidification of the space between the inner and outer walls.

Figure 9C:
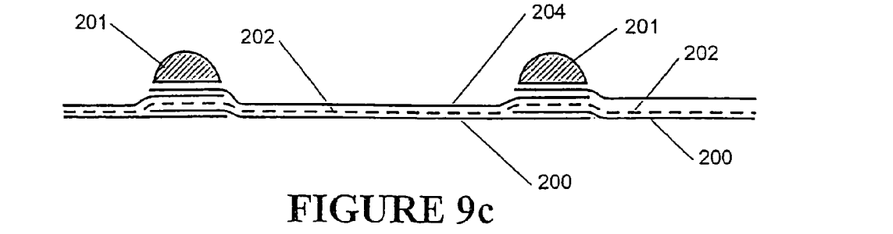

Referring to FIG. 9c the conduit of 9a is shown having breathable membrane wall 200, mesh sheath 202 and bead 201. In the embodiment of FIG. 9c a further breathable membrane sheath 204 is provided on the outside of the mesh sheath 202. The effect of this is to encapsulate the mesh 202 providing an improved aesthetic appearance and more acceptable external surface. A disadvantage of this constriction is the multitude of layers which the heat from bead 201 is required to thermally bond. Accordingly a construction of this type may require additional localised heating to thermally weld the overlapping edges of adjacent turns of membranes 200, 202, and 204.

Figure 9D:
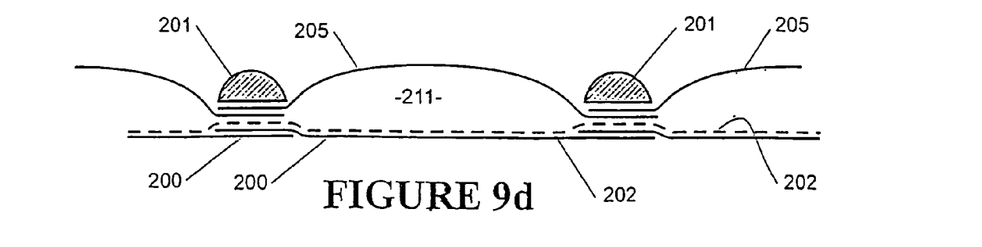

Referring to FIG. 9d a variation on the embodiment shown in FIG. 9c is depicted. In this embodiment the outer breathable membrane 205 is inflated away from the mesh membrane 202 where in FIG. 9c the outer breathable membrane 204 lay against or bonded with the mesh membrane 202. In FIG. 9d the breathable 205 is supported away from the underlying membranes 200, 202 by an inflated pocket 211. This may be considered a variant of FIG. 9b wherein the bead 201 is provided entirely on the outside of the conduit. The multitude of layers at adjoining edges poses the same forming difficulties as the embodiment of FIG. 9c.

Figure 9E:
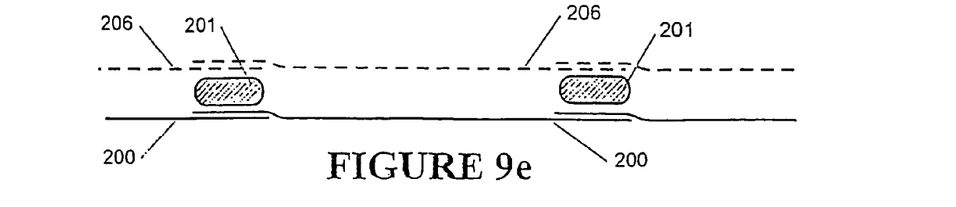

Referring to FIG. 9e a section of the conduit in which the mesh sheath is provided spaced from the breathable membrane conduit wall 200. The mesh sheath 206 is provided over the bead 201 at least in the vicinity of the joining of adjacent turns of the breathable membrane 200. Where the mesh sheath is formed from a wound tape then adjacent turns 206 of the wound tape bond over the bead 201 upon action of the heat residing in the bead 201. This embodiment reduces the number of adjacent layers required to be bonded by the bead 201 and allows the layers of breathable membrane and mesh respectively to operate independently making this tube more supple than for example for tube in FIG. 9a.

Figure 9F:
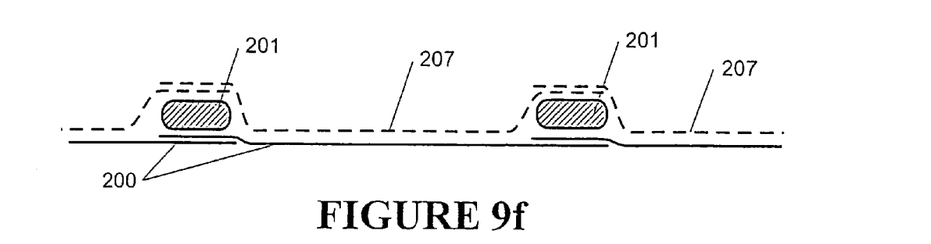

FIG. 9f is a variation of the embodiment of FIG. 9e. While an air space was provided between the mesh layer 206 and the breathable membrane layer 200 in FIG. 9e, in FIG. 9f the mesh layer 207 is shrunk, vacuumed or collapsed to lie adjacent the breathable membrane layer 200. Where one or more of the breathable membrane and mesh are formed contemporaneous with forming of the conduit then where these layers 207 and 200 meet they may bond across some or all of their contacting area. This embodiment provides the formative advantages of FIG. 9e and a construction having similar qualities to that of FIG. 9a.

Figure 9G:
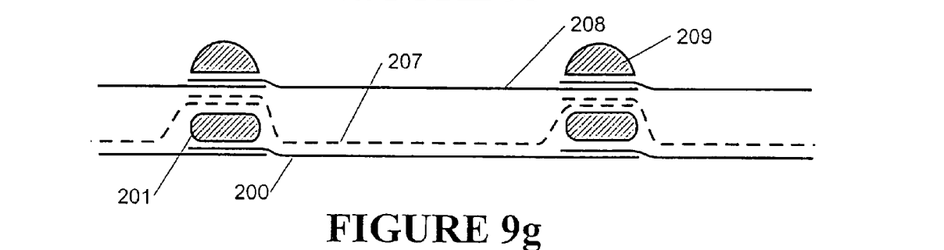

Referring to FIG. 9g, in a further embodiment, an additional breathable membrane is provided to the embodiment of FIG. 9f, spanning between turns of bead 201 and the outside of the mesh 207. To assist with bonding and for further reinforcement purposes a further bead 209 may be provided on the outside of the second breathable layer 208.

Figure 9H:
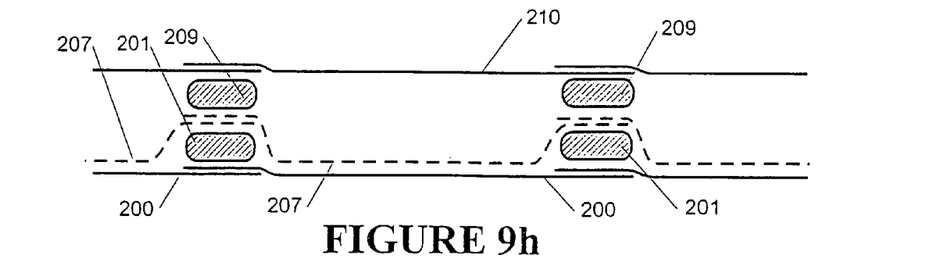

Referring to FIG. 9h a still further embodiment is shown which is a variation of the embodiment shown in FIG. 9g. In the embodiment of FIG. 9h a second layer of breathable membrane 210 is provided on the outside of second bead 209. This is instead of being between the second bead 209 and the mesh layer 207 as the second breathable layer 208 was in the embodiment FIG. 9g. This provides a larger included air space between breathable layers 202 and 210 and at any time only a double thickness of polymer, film or mesh is required to be bonded by the beads 201 or 209.

Figure 9I:
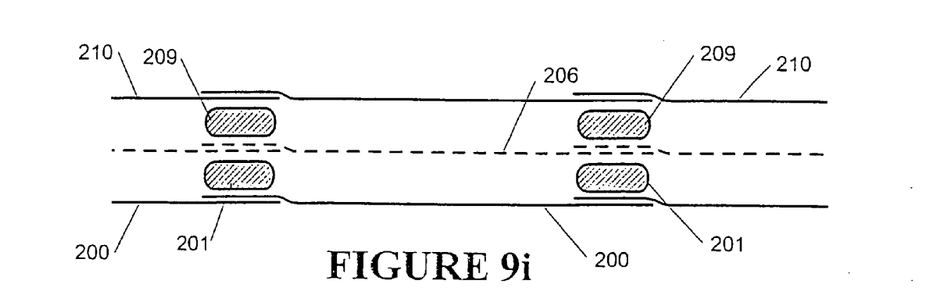

Referring to FIG. 9i a still further embodiment is shown, being a variation of the embodiment shown in 9h. In the embodiment of 9i the mesh layer 206 rather than being the deflated, collapsed or vacuumed form as in FIGS. 9f–9h, it is taut between turns of bead 201, in the fashion of 9e. This provides a pair of air spaces between the breathable layers 200 and 210, with the mesh layer 206 partially inhibiting the free air flow between the layers. However, this construction has the disadvantage that the freely suspended mesh 206 may encourage rain out in the space enclosed between the breathable membranes 200 and 210, thereby retaining liquid water within the helical wall cavity.

All of the above described configurations are considered to provide additional longitudinal reinforcement, with each having advantages and disadvantages, some of which have been specified. In forming these constructions bonding is required between some or all of the various layers, for example between the breathable membrane and one or other bead, the bead and the mesh, the mesh and breathable membrane. Accordingly, it is preferred that appropriately compatible materials are used for each element of the construction. For example while a molten polyester bead may mechanically bond adequately with nylon or polypropylene mesh a brittleness may develop and/or this impeded the simultaneous bonding of the bead with an adjacent layer of polyester based breathable membrane, for example in the embodiment of FIG. 9a. Consequently it is preferred that all three elements have the same base polymer, and for example, for a SYMPATEX® membrane which is polyester based product, a polyester bead and a mesh are preferred.

Further variations on the above embodiments may include replacement of the outer breathable layer in FIGS. 9b,c,d,g,h and i with a perforated non permeable layer, as desired. However, such variation does not provide the full insulative effect while retaining liquid vapour transmission from the insulating space to allow for further transmission through the conduit wall.

Figure 10:
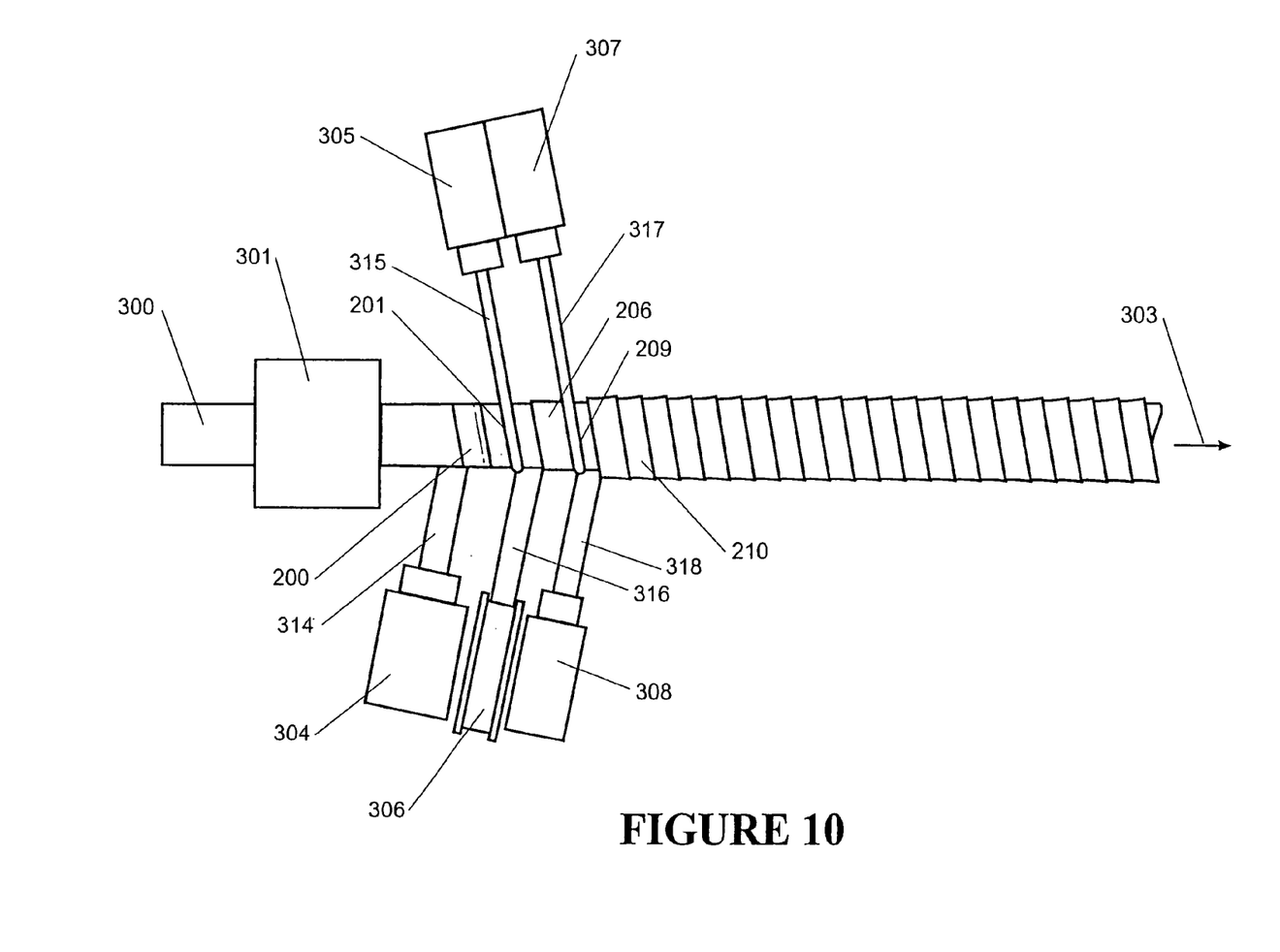
FIG. 10 is plain view of a conduit forming device for forming a reinforced twin walled conduit according to the present invention, such as the conduit depicted in FIG. 9h or 9i.

An example of forming apparatus suitable for manufacturing the product the breathing tube according to the embodiments described in FIGS. 9a–9i is shown in FIG. 10. In particular the apparatus is shown forming a conduit according to FIG. 9h or 9i. The apparatus includes a former 300 preferably of a known type including a plurality of rotating rods arranged around a central support rod. The rods extend from and are rotated by a gearbox within a machine stock 301. At least in the tube forming region the rotating rods follow a helical path. The pitch angle of the rods relative to the support rod controls the pitch angle of the tube being formed. An example of such a machine is a spiral pipeline mandrel available from OLMAS SRL of Italy. Tube being formed on the former is rotated and advanced in the direction of arrow 303 by the movement of the rotating rods. The advance speed of the former is selected relative to the rotational speed so that the pitch of the helical laying of the strip or tape on to the former 300 is a little less than the width of the strip so that adjacent turns narrowly overlap. A first extruder 304 extrudes a tape 314 of breathable polymer materials. The tape 314 deposits on the former 300 in a helical fashion by action of the former. The pitch of the helical disposition of tape 314 is slightly less than the width of tape 314. The helical deposition of tape 314 forms the inner breathable wall 200 of the conduit. A second extruder 305 extrudes a bead 315 of polymer material. The bead 315 deposits on the former over the joint or overlap between adjacent turns of tape 314 forming a raised bead 201 along this join. A tape 316 of reinforcing membrane is unrolled from a reel 306 to have edges depositing on adjacent turns of bead 201. The helically deposited reinforcing tape 316 forms reinforcing layer 206. A third extruder 307 extrudes a second molten polymer bead 317. The bead 317 is helically deposited along the overlap between adjacent turns of reinforcing tape 316. A fourth extruder 308 extrudes a second tape 318 of breathable polymer. The second tape 318 of breathable polymer is deposited on the former 300 to span between adjacent turns of second bead 317. Adjacent turns of tape 318 overlap while sufficiently molten to fuse above the second bead 209, forming outer breathable sheath 210.

In addition to the bonding of the film overlap by application of the molten bead other active fusing techniques may be applied. This may be particularly useful where a layer of longitudinal reinforcement or scrim is provided immediately adjacent the breathable film layer. Active methods may include hot air welding, hot rollers or radio frequency welding. In hot air welding a stream of hot air is blown on to the overlap of adjacent turns of breathable film, melting or fusing the adjacent edges together. This method has been found reasonably successful.

For hot roller welding a heated roller or rollers run in contact with the overlap and melt the film together. Like hot air welding hot roller welding relies on the application of a localised direct heating to the film overlap.

For radio frequency welding the film acts as an insulation layer between a pair of plates. A charge is passed between the plates melting and fusing the plastic film overlap together. The plates may take the form of a pair of rollers, one inside and one outside the tube, or a roller and one of the rotating rods of the former. Providing the plates as rollers (or as roller and forming mandrel) may render the radio frequency welding a continuous process with similar advantages to hot air welding and hot roller welding.

In a further variation on the manufacturing process the breathable film tube may be manufactured having a longitudinal seam rather than being formed as a continuous helical strip. In such an embodiment a wider web of film would be wrapped around a mandrel as it is extruded or unrolled from a reel. Longitudinal edges would overlap and be seam welded by any of the above mentioned methods. A rotary extruder may then extrude a reinforcing bead or beads on to the plastic film. Further reinforcing or film layers and helical beads may be applied by additional wrapping stations or rotating extruders as required.

Still further embodiments of a expiratory breathing conduit including longitudinal reinforcement are depicted in FIGS. 7 and 8. These embodiments utilise longitudinal reinforcing threads running parallel to the axis of the conduit.

In the embodiment of FIG. 7 the conduit includes an inner breathable polymer wall 250 with a plurality of axially extending reinforcing threads 251 running the length of said wall and spaced around the perimeter of the tube. The threads 251 are aligned parallel to one another and to the major axis of the conduit. A layer of additional longitudinal reinforcement 252, such as described earlier, and which may be a woven or non woven mesh, aligned in any suitable orientation (although preferably aligned with the principal threads running at an angle to the major axis of said conduit) encloses the breathable permeable wall and reinforcing threads. A helical bead 253 is fused or adhered to the outside of the mesh 252.

Figure 11:
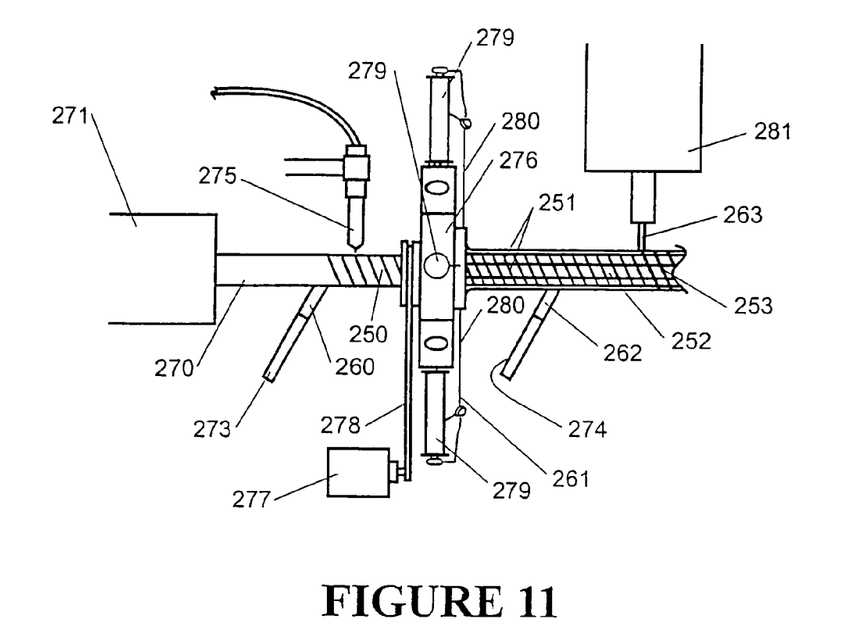
FIG. 11 is a plain view of a conduit forming device for forming a reinforced conduit according to FIG. 7.

A preferred method of forming the tube according to the embodiment of FIG. 7 is described with reference to the apparatus shown in FIG. 11. In particular in the apparatus of FIG. 11 both the inner, breathable, tube 250 and longitudinal reinforcement layer 252 are formed by helically wrapping a preformed tape or strip of the base material (breathable polymer strip 260 or mesh strip 262 respectively) on to a rotating former 270 (such as described earlier with reference to FIG. 10). The strip 260 or 262 unrolls from reels 273 and 274 respectively. Adjacent turns of breathable polymer 260 overlap at their edges. These overlapping edges are fused by thermal welding. Thermal welding is conducted as a continuous process by a hot air welding head 275. Rotation and advancement of the former 270 by the rotation head 271 continually passes the seam between adjacent turns of tape 260 past the head 275. A freely rotatable thread laying head 276 is located over the former 270 at a position between the hot air welding head 275 and the mesh spool 274. The rotating head 276 carries a plurality of spools 279 holding the reinforcing threads 251. The head 276 is rotatable by an electric motor and drive belt 277 and 278 respectively. The head 276 is preferably rotated at a speed synchronized with the speed of rotation of the former 270. Advancement of the former 270 draws thread 280 from the spools 279 to be laid as parallel threads 251 on the outside of the breathable membrane 250. The tape 262 of longitudinal reinforcement is subsequently applied over the threads 251 as a helical arrangement with edges of adjacent turns overlapping to form a continuous sheath. A bead 263 is extruded by an extruder 281 on to the overlap between adjacent turns of the mesh tape 262 to thereby form the helical reinforcing bead 253.

This embodiment of the invention provides a breathable exhalation limb reinforced against crushing by the helical bead and against longitudinal extension by the axial threads 251. The mesh sheath 252 protects the axial threads from snagging or pulling.

In the embodiment of FIG. 8 the conduit includes an inner breathable polymer wall 350. A helical bead 353 is fused or adhered to the inner breathable wall 350. A plurality of reinforcing threads 251 running the length of the wall and spaced around the perimeter of the tube are aligned parallel to one another and to the major axis of the conduit. The threads 351 are supported on the helical bead 353, with the threads spanning the spaces between turns of the helical bead. In this embodiment it is important to choose the reinforcing threads (material, gauge and number) such that the threads are sufficiently stiff to resist buckling under the transiently reduced internal pressures that could be expected during patient breathing. Unrestrained or excessive buckling of the threads could lead to unacceptable levels of conduit axial contraction. The axial threads 351 may be a spun or braided fibres, drawn or extruded mono filaments or other equivalent forms.

Figure 12:
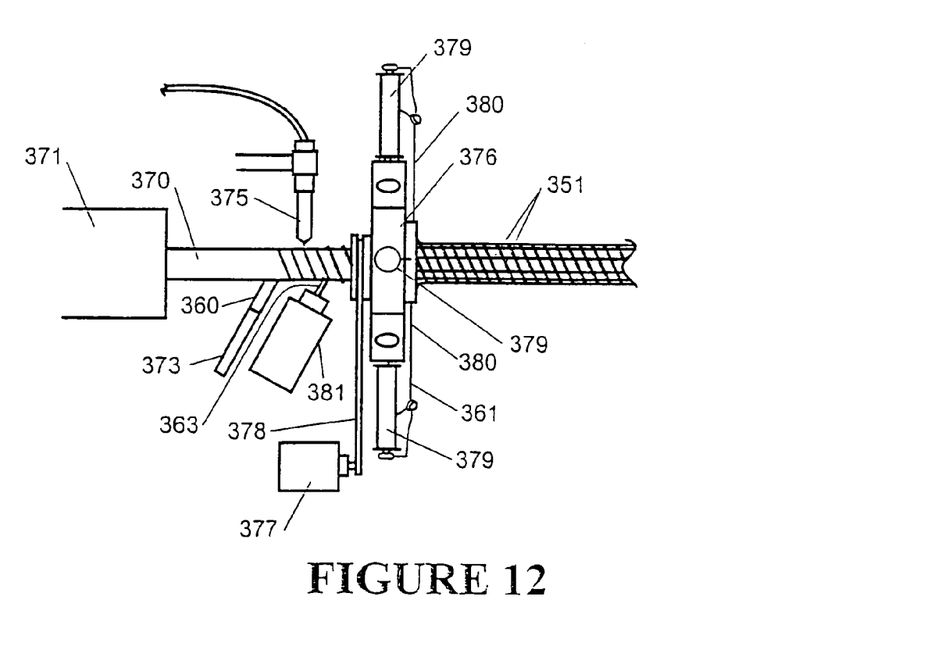
FIG. 12 is a plain view of a similar conduit forming device for forming a reinforced conduit according to FIG. 8.

A preferred method of forming the tube according to the embodiment of FIG. 8 is described with reference to the apparatus shown in FIG. 12. In particular in the machine of FIG. 12 the breathable tube 350 is formed by helically wrapping a preformed tape or strip of breathable polymer strip 360 on to a rotating former 370. The strip 360 unrolls from reels 373. Adjacent turns of breathable polymer 360 overlap at their edges. These overlapping edges are fused by thermal welding. Thermal welding is conducted as a continuous process by a hot air welding head 375. Rotation and advancement of the former 370 continually passes the seam between adjacent turns of tape 360 past the head 375. A bead 363 is extruded by an extruder 381 on to the overlap between adjacent turns of the breathable tape 362 to thereby form the helical reinforcing bead 353. A freely rotatable thread laying head 376 is located over the former after the bead extruder 381. The rotating head 376 carries a plurality of spools 379 holding the reinforcing threads 351. The head 376 is rotatable by an electric motor and drive belt 377 and 378 respectively. The head 376 is preferably rotated at a speed synchronized with the speed of rotation of the former 370. Advancement of tube along the former 370 draws thread 380 from the spools 379 to be laid as parallel threads 351 on the outside of the reinforcing bead.

This embodiment of the invention provides a breathable exhalation limb reinforced against crushing by the helical bead and against longitudinal extension by the axial threads 351. The spanning threads prevent direct contact between a user and the surface of the breathable tube, reducing the risk of punctures and the like.

It should be appreciated that with all of the forming methods involving winding of a narrow tape or strip to create a tube, it would be possible to wind two or more tapes or strips simultaneously onto the former so that the turns created by each tape are interposed by turns of other tapes, edges overlapping and being bonded together. For example a pair of tapes may be laid as a double helix. This would require a multiplication in the number of forming stations associated with the wound on components of the tube or conduit.

Figure 3:
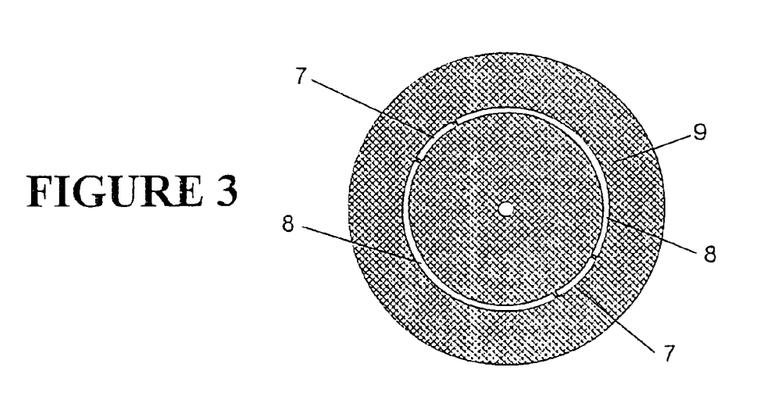
FIG. 3 is a cross sectional view of a co extrusion die head for extruding a conduit including two longitudinal strips of permeable material, similar to the conduit of FIG. 1.

Referring to FIG. 3 other forms of the conduit, such as that shown in FIG. 1, may be formed by co extrusion of the breathable material (where the material is a suitable extrudable material) with a plastic material forming the remainder of the conduit wall. A suitable co extrusion die 9 is depicted in FIG. 3 in which a pair of circumferential sections 7 of the die opening have the breathable plastic material extruded therethrough, and the remainder sections 8 of the annular extrusion opening have the non permeable plastic wall material extruded therethrough.

The purpose of the breathable region or regions of the conduit wall is to allow diffusion of water vapour from the expiratory limb of the breathing circuit along the path thereof independent of specific drain locations. This eliminates the build up of condensation within the expiratory limb by drying the humidified gases during their flow through the expiratory limb. This furthermore reduces the humidity of the gases arriving at ancillary equipment, such as filters, ventilators and the like reducing the risk of condensation accumulation, thereby improving their operation.

In accordance with a further aspect of the invention, and as exemplified in FIGS. 4 and 5 the conduit incorporating one or more longitudinal strips of breathable membrane may further be incorporated in a coaxial breathing circuit as a passive humidification device. In particular referring to the cross section in FIG. 4 the coaxial breathing circuit may include an outer conduit 11 and an inner conduit 10. Preferably, for heat transfer reasons, the inner conduit 10 carries the inspiratory flow in the space 12 there within. The expiratory flow is preferably carried in the space 13 between the inner conduit 10 and the outer conduit 11. This airflow configuration is indicated by arrows 20, 19 respectively in FIG. 5.

The inner conduit 10 is formed having one or more longitudinal strips 2, 3 of breathable membrane in the wall 1 thereof, as has previously been described with reference to FIGS. 1, 2 and 3. Thus humidity in the expiratory flow space 13 may pass through the sections 2, 3 of breathable membrane to humidify the inspiratory flow in inspiratory flow space 12.

The breathable membrane works on relative partial pressures of water vapour so, with the flows in a counter flow arrangement substantial passive humidification of the inspiratory flow can be achieved.

Referring to FIG. 5 a circuit configured including the coaxial conduit depicted in FIG. 4 is represented. In this circuit the conduit has a patient end connector 15 and a ventilator end connector 16 having inspiratory port 17 and an expiratory port 18. The inspiratory 20 and expiratory 19 counter flows are indicated.

With the coaxial conduit the ventilator may not become aware of the leak in the interior conduit. Such a leak may short circuit the patient meaning that the patient will not be supplied with sufficient oxygen. Such a short circuit may be detected by placement of a sensor at the patient end. Preferably this sensor may be located in the patient end connector 15. A short circuit closer to the ventilator will lead to continued patient rebreathing of the air volume close to the patient. This will lead to a rise in the concentration of carbon dioxide in the conduit close to the patient which can be detected directly by a $CO^2$ sensor. Such a sensor may comprise any one of a number of such sensors as is currently commercially available. Alternatively this re breathing may be detected by monitoring the temperature of the gases at the patient end connector 15, wherein a rise in temperature above a predetermined level indicates that rebreathing is occurring.

In addition to the above to reduce or eliminate the formation of condensation within either the inner or outer conduit, 10 or 11 respectively, and to maintain a substantially uniform temperature in the gases flow through the conduit, a heater means, such as a resistance heater wire, may be provided within either the inner or outer conduit, disposed within the gases spaces 12 or 13 or within the conduit walls themselves. In one possibility the heater wire may also serve as a reinforcing support (helical wire 25 in FIG. 4) within the inner conduit 10 or in the outside conduit as with coaxial conduit.

A further breathing circuit component to which the present invention can be applied is catheter mounts. A catheter mount connects between a patient interfacing component such as a mouth piece, nasal mask or endotracheal tube and the dual limbs of a breathing circuit. Connection with the dual limbs of the breathing circuit is generally via a wye connector. In the patient inhalation and exhalation cycle the dual limbs of the breathing circuit each have a distinct role, one as inhalation conduit and one as exhalation conduit. The catheter mount serves a dual role, transporting both inhaled and exhaled gases. Accordingly, the catheter mount can have significant disadvantages. A volume of exhaled air remains in the catheter mount between exhalation and inhalation. Accordingly some air is re-breathed by the patient. While not unacceptable, rebreathing is not generally desirable and where significant rebreathing is likely, a boost in oxygen supply levels may be required.

Gases inhaled by a patient are, in a well managed ventilation system, delivered in a condition having humidity near a saturation level and at close to body temperature, usually at a temperature between 33° C. and 37° C. This temperature may be maintained by a heater in the inhalation conduit right up to the point where the gases enter the catheter mount. Gases exhaled by a patient are returned fully saturated and are subjected to further cooling as they flow through the catheter mount. Accordingly, although little condensation forms on the interior walls during patient inhalation, significant condensation levels may form during patient exhalation. The condensation, or rain out, occurring inside the catheter mount is particularly deleterious due to its proximity to the patient. Mobile condensate breathed or inhaled by a patient may lead to coughing fits or other discomfort.

Figure 13:
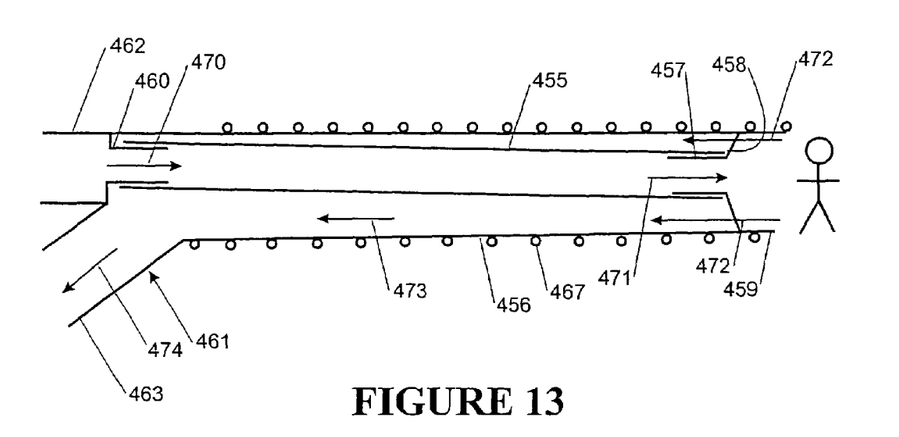
FIG. 13 is a cross sectional side elevation of a catheter mount incorporating the present invention.

A catheter mount incorporating the present invention is depicted in FIG. 13. The catheter mount incorporates the wye connector at the ventilator end. An internal conduit 455 extends coaxially with the outer conduit 456. The internal conduit 455 is supported at its patient end on a internal conduit connector 457 which is turn is supported via support struts 458 from patient end connector 459. The inner conduit 455 is supported at its other end on an inner conduit connector 460 which forms part of the ventilator end connector 461.

In the catheter mount of FIG. 13 the ventilator end inner conduit connector 460 communicates with the inspiratory conduit connector 462. The outer conduit 456 has at least a part of its wall being made from a breathable material. Preferably the outer conduit 456 is formed entirely from breathable material, and may also include lateral reinforcement (a spiral reinforcing bead 467) and longitudinal reinforcement (axially oriented threads 490) on the outside thereof. When constructed according to the manner earlier described with respect to FIGS. 12 and 8 the spiral bead 467 is laid on the overlap between consecutive turns of the extruded tape and assists fusion of the overlap and reinforcement against crushing.

Therefore in use the catheter mount according to FIG. 13 has an inspiratory flow entering the catheter mount as indicated by arrow 470. The inspiratory flow passes through the inner conduit to exit to the patient through the patient end connector 459 as indicated by arrows 471. Upon patient exhalation, whether assisted or otherwise, expired gases pass through connector 459 and into the space surrounding the inner conduit 455 as indicated by arrows 472. These gases pass along the inside of the wall of outer conduit 456 as indicated by arrows 473 and out through the expiratory tube connector 463 of ventilation connector 461 as indicated by arrow 474. In passing through the catheter mount within the space between the inner conduit 455 and the outer wall 456 water vapour may pass through the water vapour permeable portions of the outer conduit 456. Preferably the entire of outer conduit 456, apart from any reinforcing rib, is breathable. In this way, although the expired gases may experience some temperature drop as they pass through the catheter mount to the expiratory conduit connector 463, hand in hand with this temperature drop is a reduction in humidity by water vapour passing through the breathable membrane of the outer conduit. Accordingly, relative saturation of the expiratory flow is reduced and rain out is reduced.

The catheter mount incorporating features according to the present invention includes explicit division of the inspiratory and expiratory flows through the catheter mount—significantly reducing rebreathing. Rain out is also reduced by reducing the humidity of the expired gases even as the temperature of those gases reduces.

While some embodiments of the present invention have been described as preferred and convey particular advantages over other embodiments many other combinations may prove commercially useful.

The invention claimed is:

1. A limb for a breathing circuit comprising:
   an inlet,
   an outlet, and
   an enclosing wall defining a substantially singular exhalation flow passage between said inlet and said outlet, at least a region of said enclosing wall being of a material that allows the passage of water vapour without allowing the passage of liquid water or respiratory gases
   a water vapour flow path from said exhalation flow passage to ambient air through said material, and
   wherein said limb is an expiratory limb of the breathing circuit.

2. A limb for a breathing circuit as claimed in claim 1 wherein said material is selected from:
   (a) hydrophilic thermoplastics,
   (b) perfluorinated polymers,
   (c) woven treated fabrics.

3. A limb for a breathing circuit as claimed in claim 1 wherein said material is a perfluorinated polymer membrane.

4. A limb for a breathing circuit as claimed in claim 1 wherein said material is a hydrophilic polyester block copolymer.

5. A limb for a breathing circuit as claimed in claim 1 wherein said flow passage is a conduit and said region or regions is or are distributed over the length of said conduit.

6. A limb for a breathing circuit as claimed in claim 5 wherein said region or regions are elongate and run at least a substantial part of the length of said conduit.

7. A limb for a breathing circuit as claimed in claim 5 including a series of said regions spaced along the length of said conduit.

8. A limb for a breathing circuit as claimed in claim 5 wherein said conduit including said regions is extruded.

9. A limb for a breathing circuit as claimed in claim 8 wherein the entire of said extruded conduit is of a material that allows the passage of water vapour without allowing the passage of liquid water or respiratory gases.

10. A limb for a breathing circuit as claimed in claim 8 wherein said regions of a material that allows the passage of water vapour without allowing the passage of liquid water or respiratory gases are one or more longitudinal strips running the complete length of said conduit.

11. A limb for a breathing circuit as claimed in claim 5 wherein said conduit includes at least one helically wound polymer tape or strip, part or all of said strip being of a material that allows the passage of water vapour without allowing the passage of liquid water or respiratory gases, respective edges of adjacent turns of said strip being adjoining or overlapping and bonded.

12. A limb for a breathing circuit as claimed in claim 11 including lateral reinforcement against crushing wherein said lateral reinforcement is a helical bead disposed over said adjoining or overlapping edges between turns of strip.

13. A limb for a breathing circuit as claimed in claim 5 wherein said conduit includes at least one longitudinal strip, part or all of said strip being of a material that allows the passage of water vapour without allowing the passage of liquid water or respiratory gases, said strip or strips extending parallel to the axis or said conduit, edges of said strip or strips adjoining or overlapping to form an enclosed tube and bonded.

14. A limb for a breathing circuit as claimed in claim 5 wherein said conduit is a blown film tube of a material that allows the passage of water vapour without allowing the passage of liquid water or respiratory gases.

15. A limb far a breathing circuit as claimed in any one of claims 10 to 14 including lateral reinforcement against crushing.

16. A limb for a breathing circuit as claimed in claim 15 wherein said lateral reinforcement includes a plurality of annular corrugations distributed over the length of said conduit.

17. A limb for a breathing circuit as claimed in claim 15 wherein said lateral reinforcement is a helical bead or a series of annular ring beads or ribs distributed over the length of said conduit.

18. A limb for a breathing circuit as claimed in claim 4 wherein said lateral reinforcement is a skeletal reinforcing structure within said conduit.

* * * * *

UNITED STATES PATENT AND TRADEMARK OFFICE
CERTIFICATE OF CORRECTION

| | |
|---|---|
| PATENT NO. | : 7,140,366 B2 |
| APPLICATION NO. | : 10/622755 |
| DATED | : November 28, 2006 |
| INVENTOR(S) | : Smith et al. |

It is certified that error appears in the above-identified patent and that said Letters Patent is hereby corrected as shown below:

Title page, item
(73) Assignee: "Fisher & Payke Healthcare Limited" should be
--Fisher & Paykel Healthcare Limited --

Column 14, Line 14 "as claimed in claim 4" should be
-- as claimed in claim 14 --

Signed and Sealed this

Tenth Day of April, 2007

JON W. DUDAS
*Director of the United States Patent and Trademark Office*